US012724107B2

(12) United States Patent
Zhan

(10) Patent No.: US 12,724,107 B2
(45) Date of Patent: Sep. 1, 2026

(54) WIFI-BASED HUMAN BODY DETECTION METHOD, AND SMART DEVICE

(71) Applicant: ESPRESSIF SYSTEMS (SHANGHAI) CO., LTD., Shanghai (CN)

(72) Inventor: Zhaocheng Zhan, Shanghai (CN)

(73) Assignee: ESPRESSIF SYSTEMS (SHANGHAI) CO., LTD., Shanghai (CN)

( * ) Notice: Subject to any disclaimer, the term of this patent is extended or adjusted under 35 U.S.C. 154(b) by 441 days.

(21) Appl. No.: 18/261,052

(22) PCT Filed: Jan. 11, 2022

(86) PCT No.: PCT/CN2022/071354
§ 371 (c)(1),
(2) Date: Dec. 26, 2023

(87) PCT Pub. No.: WO2022/148477
PCT Pub. Date: Jul. 14, 2022

(65) Prior Publication Data

US 2024/0319318 A1 Sep. 26, 2024

(30) Foreign Application Priority Data

Jan. 11, 2021 (CN) ......................... 202110029206.7

(51) Int. Cl.
*G01S 7/00* (2006.01)
*A61B 5/05* (2021.01)
(Continued)

(52) U.S. Cl.
CPC ................ *G01S 7/006* (2013.01); *A61B 5/05* (2013.01); *A61B 5/1118* (2013.01);
(Continued)

(58) Field of Classification Search
CPC ...... G01S 7/006; G01S 7/4021; G01S 13/003; G01S 13/56; A61B 5/05; A61B 5/1118; A61B 2560/0233
(Continued)

(56) References Cited

U.S. PATENT DOCUMENTS 10,826,629 B1 11/2020 Lu et al.
2003/0112882 A1 6/2003 Sampath
(Continued)

FOREIGN PATENT DOCUMENTS

CN 102883360 A 1/2013
CN 103023589 A 4/2013
(Continued)

OTHER PUBLICATIONS

Zhao, Zhi-jin et al., A Channel Estimation Method for OFDM Based on Forward Averaging and Time Domain Filtering, Computer Simulation Sep. 15, 2007.
(Continued)

*Primary Examiner* — Brady W Frazier
(74) *Attorney, Agent, or Firm* — Aird & McBurney LP

(57) ABSTRACT

The present disclosure provides a Wi-Fi based human body detection method, which includes selecting a sub-carrier data source device by a smart device, acquiring sub-carrier channel frequency responses, checking and filtering out invalid sub-carrier channel frequency responses, obtaining sub-carrier amplitudes, and grouping to obtain a plurality of datasets. Each data set is divided into multiple sub-datasets according to different parts of the sub-carrier channel frequency responses, and then for each sub-dataset, a correlation coefficient between the sub-carrier amplitudes is calculated, to obtain a human body presence detection value; a Mahalanobis distance or a Euclidean distance between the sub-carrier amplitudes is calculated to obtain a human
(Continued)

activity detection value; in conjunction of a human activity threshold and a human presence threshold, a state of a human body sign is determined and reported to a cloud server. The present disclosure also includes a smart device for implementing the above method.

20 Claims, 7 Drawing Sheets

(51) Int. Cl.
*A61B 5/11* (2006.01)
*G01S 7/40* (2006.01)
*G01S 13/00* (2006.01)
*G01S 13/56* (2006.01)

(52) U.S. Cl.
CPC .......... *G01S 7/4021* (2013.01); *G01S 13/003* (2013.01); *G01S 13/56* (2013.01); *A61B 2560/0223* (2013.01)

(58) Field of Classification Search
USPC .......................................................... 342/52
See application file for complete search history.

(56) References Cited

U.S. PATENT DOCUMENTS

| | | | |
|---|---|---|---|
| 2010/0008406 | A1 | 1/2010 | Sawai et al. |
| 2016/0235302 | A1 | 8/2016 | Melodia et al. |
| 2018/0262283 | A1 | 9/2018 | Guarin Aristizabal et al. |
| 2018/0365975 | A1* | 12/2018 | Xu ...................... G08B 29/185 |
| 2019/0325209 | A1 | 10/2019 | Liu et al. |
| 2019/0379467 | A1 | 12/2019 | Neumeier et al. |
| 2020/0030612 | A1* | 1/2020 | Song .................. A61N 1/36521 |
| 2020/0163590 | A1 | 5/2020 | Lin et al. |
| 2020/0408875 | A1 | 12/2020 | Mai et al. |
| 2022/0413120 | A1* | 12/2022 | Va .......................... G01S 13/42 |
| 2022/0413125 | A1* | 12/2022 | Aliakseyeu ............. G01S 13/04 |

FOREIGN PATENT DOCUMENTS

| | | | |
|---|---|---|---|
| CN | 103596266 | A | 2/2014 |
| CN | 104267439 | A | 1/2015 |
| CN | 104467991 | A | 3/2015 |
| CN | 104502982 | A | 4/2015 |
| CN | 104883732 | A | 9/2015 |
| CN | 106411433 | A | 2/2017 |
| CN | 106658590 | A | 5/2017 |
| CN | 106792808 | A | 5/2017 |
| CN | 106971474 | A | 7/2017 |
| CN | 108038419 | A | 5/2018 |
| CN | 108197612 | A | 6/2018 |
| CN | 108332361 | A | 7/2018 |
| CN | 108833036 | A | 11/2018 |
| CN | 109033979 | A | 12/2018 |
| CN | 109084774 | A | 12/2018 |
| CN | 109658655 | A | 4/2019 |
| CN | 109671238 | A | 4/2019 |
| CN | 109998549 | A | 7/2019 |
| CN | 110113116 | A | 8/2019 |
| CN | 110149604 | A | 8/2019 |
| CN | 110337066 | A | 10/2019 |
| CN | 110706463 | A | 1/2020 |
| CN | 110730473 | A | 1/2020 |
| CN | 111225354 | A | 6/2020 |
| CN | 111481203 | A | 8/2020 |
| CN | 111657897 | A | 9/2020 |
| CN | 112869734 | A | 6/2021 |
| JP | 2019148428 | A | 9/2019 |

OTHER PUBLICATIONS

Yang, Xiaolong et al., Indoor Through-the-wall Passive Human Target Detection Algorithm, Journal of Electronics & Information Technology, 42(03) Mar. 15, 2020.

Quinghua, Yao et al., Lightweight behavior recognition method based on CSI, Application Research of Computers, 35(11) Dec. 12, 2017.

* cited by examiner

WIFI-BASED HUMAN BODY DETECTION METHOD, AND SMART DEVICE

CROSS-REFERENCE TO RELATED APPLICATIONS

This application is the U.S. National Phase Application under 35 U.S.C. § 371 of International Patent Application No. PCT/CN2022/071354 filed on Jan. 11, 2022, which claims priority to Chinese Patent Application CN202110029206.7 filed on Jan. 11, 2021. The disclosures of the aforementioned applications are hereby incorporated by reference in their entireties.

TECHNICAL FIELD

The application relates to the technical field of detecting a human body sign, in particular to a Wi-Fi based human body detection method and a smart device therefor.

BACKGROUND ART

Human behavior recognition is a technology that uses computer technology to automatically detect, analyze and understand body movements. It is widely used in emerging fields such as smart home, security monitoring, medical rehabilitation, and human-computer interaction. Human behavior recognition can generally be divided into two categories: contact type and non-contact type. Wearable devices are the key carriers of contact type behavior recognition systems, but there are many limitations such as expensive devices, inconvenience for users to wear, and intrusion of attention. Non-contact type behavior recognition can provide device-free sensing services and user-friendly interactions, and therefore has received extensive attention from researchers.

Current non-contact type behavior recognition mainly relies on depth cameras and radio signals. However, the popularity of the former is limited by lighting conditions, line-of-sight path interference, monitor dead spots, and privacy issues; while the latter usually requires the deployment of dedicated experimental equipment, making it difficult to be promoted on a large scale. As urban infrastructure, the wireless signals provided by commercial Wi-Fi devices have the advantages of ubiquity, ease of use, high cost-effectiveness, and long transmission distance etc., and have received wide attention in the field of human behavior recognition in recent years, where early work is to realize simple indoor human motion detection based on Wi-Fi received signal strength (RSS). In order to further improve the sensing granularity and recognition accuracy, researchers have started to extract channel state information (CSI) at the physical layer from Wi-Fi commercial network interface cards (NICs). CSI can describe the multipath link changes caused by a sensed target, so as to use the amplitude and phase information at the sub-carrier level to achieve more complex and fine-grained behavior recognition, such as indoor activity monitoring, fall detection, gait authentication and gesture recognition. However, most methods require extensive professional knowledge and domain experience to guide model design, signal mining and feature selection when establishing the mapping relationship between Wi-Fi signal disturbance and human behavior, which makes the system less stable, less practical and less accurate overall. How to achieve robust, ubiquitous, and highly accurate human behavior recognition using minimal human intervention has become an urgent problem to be solved.

SUMMARY

The purpose of the present disclosure is to provide a Wi-Fi based human body detection method, which mainly solves the problems in the above-mentioned existing art. It is a Wi-Fi based human body detection method and a smart device with high reliability and good user experience to solve the problems raised in the background art above.

In order to achieve the above objectives, the technical solution adopted by the present disclosure is to provide a Wi-Fi based human body detection method, which is applied to detect a human body sign in an environment by using a change of the sub-carrier channel frequency responses in the channel state information of a Wi-Fi connection of the smart device, and includes the below.

In a plurality of detection environments, the smart device selects a sub-carrier data source device, acquires the sub-carrier channel frequency responses of the sub-carrier data source device, checks and filters out invalid sub-carrier channel frequency response, and then stores the sub-carrier channel frequency responses.

The smart device obtains sub-carrier amplitudes from the stored sub-carrier channel frequency responses, and obtains a plurality of data sets by grouping the sub-carrier amplitudes; divides each of the plurality of data sets into a plurality of sub-datasets based on different parts of the sub-carrier channel frequency responses, and then for each of the sub-datasets, a correlation coefficient between the sub-carrier amplitudes contained in the same sub-dataset is calculated to form a sub-dataset correlation coefficient vector, and a Mahalanobis distance between the sub-carrier amplitudes contained in the same sub-dataset is calculated to form a sub-dataset distance vector.

And then, an average of variances of a plurality of sub-dataset correlation coefficient vectors is obtained and taken as a human activity detection value, and an average of the variances of the plurality of the sub-datasets distance vectors is obtained and taken as a human presence detection value; in response to the human activity detection value being greater than a human activity threshold, it is determined as a state of human activity; in response to the human presence detection value being smaller than a human presence threshold, it is determined as a state of human presence, otherwise it is determined as a state of human absence.

Further, in response to the smart device determining the state of human activity, the smart device reports the state of human activity to a cloud server.

Further, in response to the smart device detecting a change between the state of human presence and the state of human absence, the smart device reports the state of human presence to the cloud server.

Further, when the smart device generates the sub-dataset distance vector, the smart device forms the sub-dataset distance vector by calculating a Euclidean distance between the sub-carrier amplitudes included in the same sub-dataset.

Further, the smart device checks and filters out invalid sub-carrier channel frequency responses, which further includes: the smart device calculates the distance between first three sub-carrier amplitudes in different parts of the sub-carrier channel frequency responses, and in response to the distance being greater than a distance threshold, it is determined that the sub-carrier channel frequency response is invalid.

Further, the distance threshold is 8.

Further, each of the data sets includes 50 sub-carrier amplitudes.

Further, the detection environment includes a smart device and a wireless access point as a sub-carrier data source; the smart device continuously sends Ping packets to the wireless access point, and receives the sub-carrier channel frequency response carried in Ping Replay packets returned by the wireless access point.

Further, the detection environment includes a plurality of smart devices and a wireless access point as a sub-carrier data source; the smart device continuously sends Ping packets to the wireless access point, and receives from the wireless access point the sub-carrier channel frequency responses carried in Ping Replay packets returned by other smart devices.

Further, the detection environment includes one or more smart devices and a packet-sending device as a sub-carrier data source; the packet-sending device constantly switches channels and continuously sends Ping packets; the smart device acquires the sub-carrier channel frequency response from the Ping packets.

Further, a process of selecting the sub-carrier data source device by the smart device is included, which includes the following.

The smart device turns on a hybrid mode, and binds the wireless access point as the sub-carrier data source device by default; in response to the smart device receiving data from a packet-sending device, the smart device binds the packet-sending device as the sub-carrier data source device; in response to the smart device receiving a binding command from the cloud server, the smart device binds a device specified in the binding command as the sub-carrier data source device.

Further, the method also includes a sub-carrier selection process; the smart device only groups the sub-carrier amplitudes corresponding to the sub-carriers selected by the sub-carrier selection process, and puts them into the data set; in response to the smart device detecting a change of the sub-carrier data source device, or receiving a sub-carrier filtering request command initiated by the cloud server, the smart device starts the sub-carrier selection process, and the sub-carrier selection process including the following.

In response to there being no human presence in the environment, the smart device collects the sub-carrier channel frequency responses for multiple times for each sub-carrier, and forms the sub-carrier amplitude vector based on the sub-carrier amplitudes corresponding to the sub-carrier channel frequency responses of each time, and then forms a sub-carrier amplitude matrix from all the sub-carrier amplitude vectors; reduces the sub-carrier amplitude matrix into a one-dimensional principal component vector by using a principal component analysis algorithm; calculates a correlation coefficient between each of the sub-carrier amplitude vectors and the principal component vector, and in response to the correlation coefficient being greater than a valid sub-carrier threshold, determines the corresponding sub-carrier as a valid sub-carrier.

Further, the smart device collects the sub-carrier channel frequency responses for 500 times for each sub-carrier.

Further, the method also includes a threshold calibration method for automatically calibrating the human activity threshold and the human presence threshold in different scenarios, including the following.

In response to there being no human presence in the environment, the smart device enters an automatic calibration mode when the smart device receives a threshold calibration start command from the cloud server; in the automatic calibration mode, the smart device does not perform the human body sign detection; after entering the automatic calibration mode, the smart device records and continuously calculates the human activity detection value and the human presence detection value, and stores the maximum value of the human activity detection value and the minimum value of the human presence detection value until receiving a threshold calibration stop command initiated by the cloud server; after receiving the threshold calibration stop command, the smart device sets a new human activity threshold and a new human presence threshold; the new human activity threshold is greater than the maximum value of the human activity detection value, and the new human presence threshold is smaller than the minimum value of the human presence detection value.

Further, the new human activity threshold is the maximum value of the human activity detection value increased by 10%, and the new human presence threshold is the minimum value of the human presence detection value decreased by 10%.

The present disclosure also includes a smart device, including: a processor, a memory, and a Wi-Fi transceiver module, wherein the memory stores a program, and the program when being executed by the processor, implementing the steps of the above-mentioned human body detection method.

In view of the above technical features, the disclosure has the following advantages:

1. More CSI information is obtained based on the embedded MCU. The embedded MCU such as ESP32 and ESP32-S2 used in the present disclosure can obtain more low-level Wi-Fi CSI signals and can obtain all sub-carrier data. Up to 306 sub-carriers can be obtained, and the current RF base noise, receiving time and antenna can also be obtained. The present disclosure optimizes the algorithm and removes redundant calculations.
2. Less CPU performance is taken up as the method can be run directly on the embedded MCU. The present disclosure is used to add the function to existing smart devices such as smart lights and smart homes, which has lower cost and wider application range, and the response time of the devices is improved through edge computing.
3. The present disclosure sets different detection ways according to different scenarios, including a first way that can complete human body detection when there is only one smart device in the environment and there is a wireless access point in the detection environment; a second way that is suitable for the environment with two or more smart devices and do not depend on the location of the wireless access point, and is not affected by other devices accessing the wireless access point; and a third way that uses a dedicated packet-sending device to achieve high accuracy detection, which is completely free from the influence of the wireless access point.
4. The present disclosure introduces sub-carrier filtering, uses PCA principal component analysis to filter out invalid sub-carrier data, thereby eliminating the influence of invalid sub-carriers on the results and thus improving the accuracy of human body detection.
5. The present disclosure can automatically calibrate the threshold value according to different usage scenarios, effectively improve the stability of the device, and eliminate the impact on sub-carriers due to different environments, placement of Wi-Fi antennas, and product shapes.

6. The present disclosure detects the human body sign by using the correlation coefficient and the Mahalanobis distance or the Euclidean distance between the sub-carriers, so that the interference in the environment can be effectively filtered, because both the correlation coefficient and the Mahalanobis distance are related to the principal components of the sub-carriers at the corresponding time. In particular, in combination with principal component analysis, errors can be effectively reduced.

In the figures: 100—cloud server, 200—wireless access point, 300—smart device, 400—packet-sending device, 500—processor, and 600—storage.

DETAILED DESCRIPTION OF THE PREFERRED EMBODIMENTS

The disclosure will be further described in the following with reference to the specific embodiments. It should be understood that these embodiments are only used to illustrate the disclosure and not to limit the scope of the disclosure. In addition, it should be understood that those skilled in the art can make various changes or modifications to the disclosure after reading the content taught by the disclosure, and these equivalent forms also fall within the scope defined by the appended claims of the disclosure.

Figure 1:
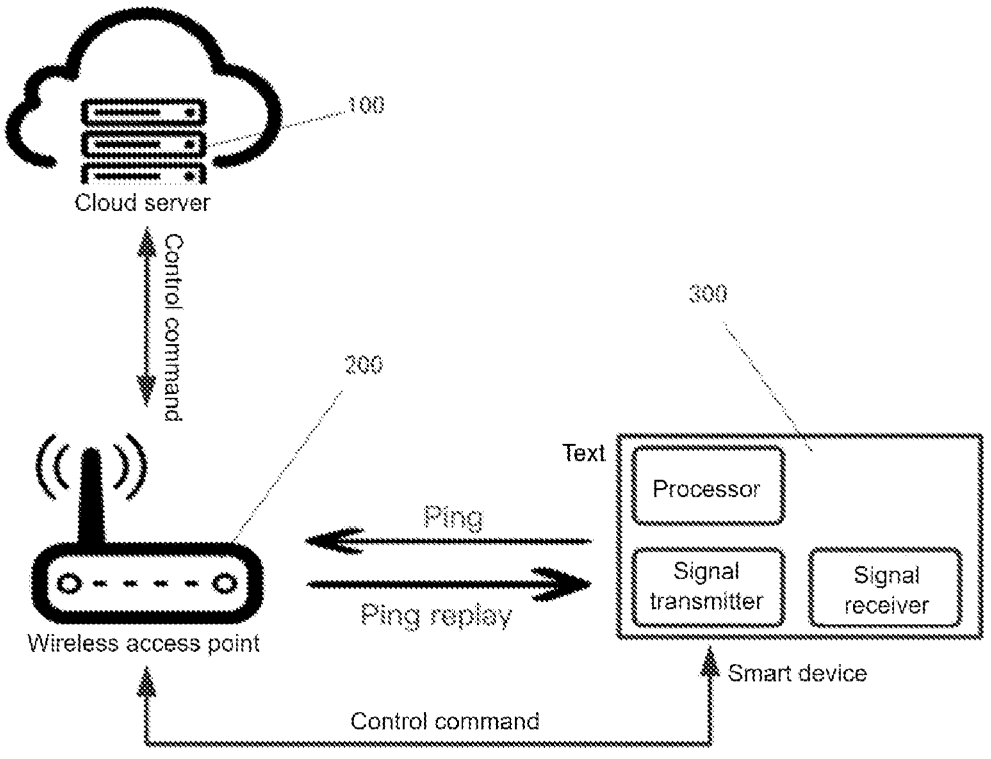
FIG. 1 is a schematic diagram of a system in a preferred embodiment of a Wi-Fi based human body detection method according to the present disclosure.

Referring to FIG. 1, the present disclosure discloses a preferred embodiment of a Wi-Fi based human body detection method, which includes a cloud server 100, a wireless access point 200, and a smart device 300. The smart device 300 communicates with the cloud server 300 through the wireless access point 200, receives control commands from the cloud server 300 and feeds back execution results, or actively reports state information. The smart device 300 uses the changes of a sub-carrier channel frequency response in the channel state information of a Wi-Fi connection (for example, the sub-carrier channel frequency response information contained in the Ping packets and the Ping replay packets between the smart device 300 and the wireless access point 200) to detect human body signs in an environment, including whether there is a person (human presence) or whether there is human movement (human activity).

The Wi-Fi based human body detection method of the present disclosure can select a sub-carrier data source device according to different detection environments. Different detection environments are used to meet different needs, including three typical scenarios.

Figure 2:
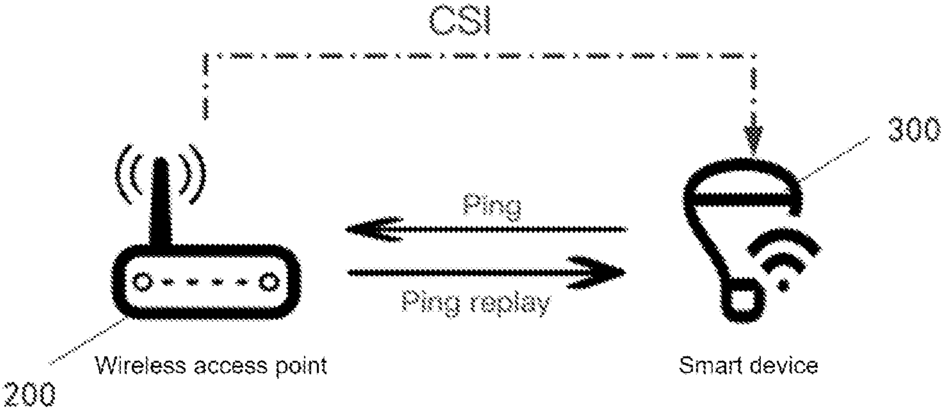
FIG. 2 is a schematic diagram of a first detection environment in a preferred embodiment of the Wi-Fi based human body detection method according to the present disclosure.

As shown in FIG. 2, the first detection environment includes a smart device 300 and a wireless access point 200 as a source of sub-carrier data. The smart device 300 continuously sends Ping packets to the wireless access point 200, and then receives the Ping Replay packets returned by the wireless access point 200, and obtains information from the sub-carrier channel frequency response carried in the Ping Replay packets, and completes the human body sign detection. In the first detection environment, only one smart device 300 and the wireless access point 200 are needed to complete the configuration, which is simple and convenient. However, the first detection environment depends on the specific status of the wireless access point 200, for example, the location of the wireless access point 200, the supported Wi-Fi protocols, etc. may affect the result of the human body sign detection.

Figure 3:
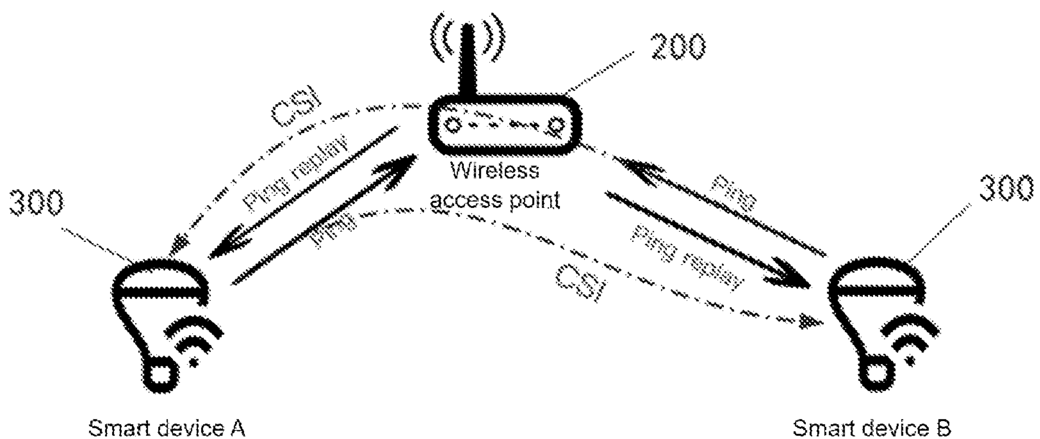
FIG. 3 is a schematic diagram of a second detection environment in a preferred embodiment of the Wi-Fi based human body detection method according to the present disclosure.

As shown in FIG. 3, the second detection environment includes a plurality of smart devices 300 and one wireless access point 200 as a source of sub-carrier data. The smart device 300 continuously sends Ping packets to the wireless access point, and receives the Ping Replay packets returned by other smart devices 300 from the wireless access point 200, uses the sub-carrier channel frequency response carried in the Ping Replay packets to obtain information, and completes the human body sign detection. The second detection environment is a supplement to the first detection environment. It does not depend on the location of the wireless access point 200, and is not affected by other network devices connected under the wireless access point 200, but still depends on the specific state of the wireless access point 200, for example, the Wi-Fi protocols supported by the wireless access point 200, etc. may affect the result of the human body sign detection.

Figure 4:
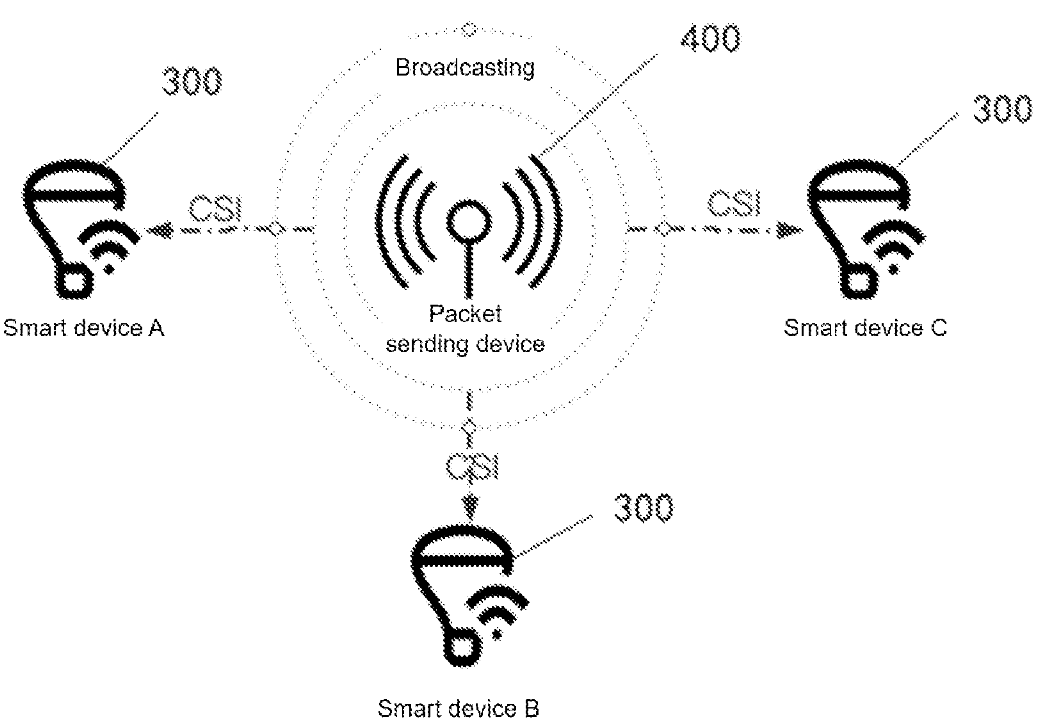
FIG. 4 is a schematic diagram of a third detection environment in a preferred embodiment of the Wi-Fi based human body detection method according to the present disclosure.

As shown in FIG. 4, the third detection environment includes one or more smart devices 300 and a packet sending device 400 as a source of sub-carrier data. The packet-sending device 400 is a dedicated hardware, which constantly switches channels and continuously sends Ping packets on different channels. Each smart device 300 obtains the sub-carrier channel frequency responses from the Ping packets sent by the packet-sending device 400 to complete the human body sign detection. The detection in the third detection environment is completed without being affected by the wireless access point, and the detection accuracy and reliability are the highest. In particular, when there are multiple network devices in the environment, only one packet-sending device 400 is continuously sending packets, which causes little interference to the network environment. The packet-sending device 400 directly uses the interface of the data link layer, without the need for operations such as provisioning and binding to the wireless access point, and can send packets without establishing a connection, which eliminates the packet headers of the network layer and transport layer, making the packets smaller and reducing the impact on the surrounding network. However, to configure the third detection environment, in addition to setting up ordinary smart devices 300, it is also necessary to add a packet-sending device 400 specially for sending packets, and therefore the cost is relatively high.

Figure 5:
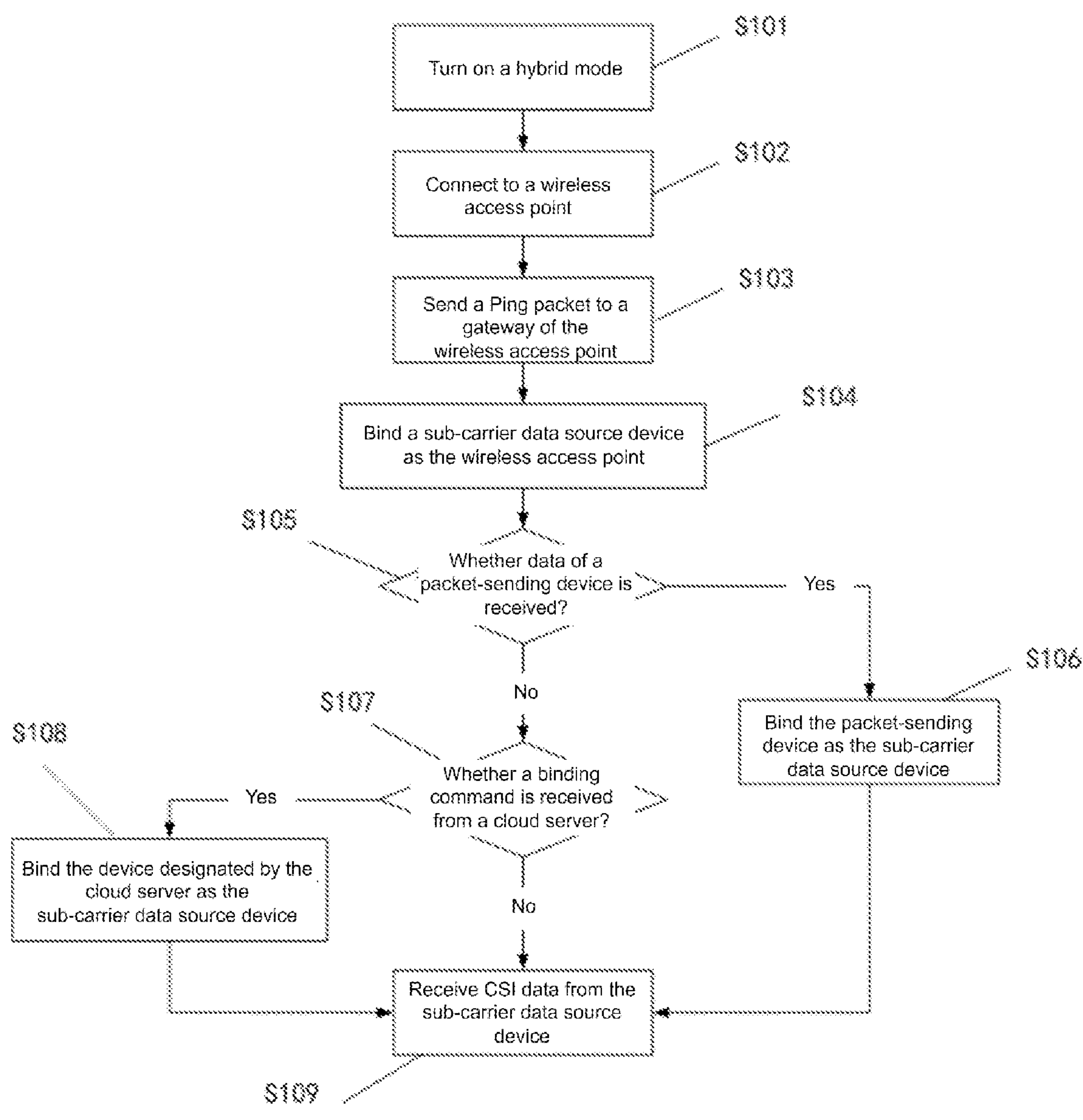
FIG. 5 is a flow chart of a selected sub-carrier data source device in a preferred embodiment of the Wi-Fi based human body detection method according to the present disclosure.

FIG. 5 illustrates a flow chart of a method for a smart device to select a sub-carrier data source device. In some embodiments, when the detection environment contains multiple wireless access points or further contains a packet-sending device, the smart device can select the sub-carrier data source device for human body sign detection according to the following process, in which case, the smart device can preferentially select the packet-sending device as the sub-carrier data source device.

The method includes the following steps.

The smart device first turns on a hybrid mode (step S101), then connects to the wireless access point (step S102), and sends a Ping packet to a gateway of the wireless access point (step S103). If the wireless access point supports the Ping packet, it will send a Ping relay packet in response to the Ping packet. After receiving the Ping relay packet, the smart device binds the wireless access point as the sub-carrier data source device (step S104), analyzes the sub-carrier channel frequency response carried in the Ping relay packet returned by the wireless access point, and executes the human body sign detection (step S109).

If the smart device receives a Ping packet from the packet-sending device through the hybrid mode (step S105), the smart device stops sending the Ping packet to the wireless access point, binds the packet-sending device as the sub-carrier data source device (step S106), and analyzes the sub-carrier channel frequency response carried in the data packet sent by the packet-sending device, and executes the human body sign detection (step S109).

If the smart device does not receive a Ping packet from the packet-sending device, the smart device monitors whether a binding command is received from a cloud server (step S107), then binds the device designated by the cloud server as the sub-carrier data source device (step S108), analyzes the sub-carrier channel frequency response carried in the data packet sent by the device designated by the cloud server, and executes the human body sign detection (step S109).

Figure 6:
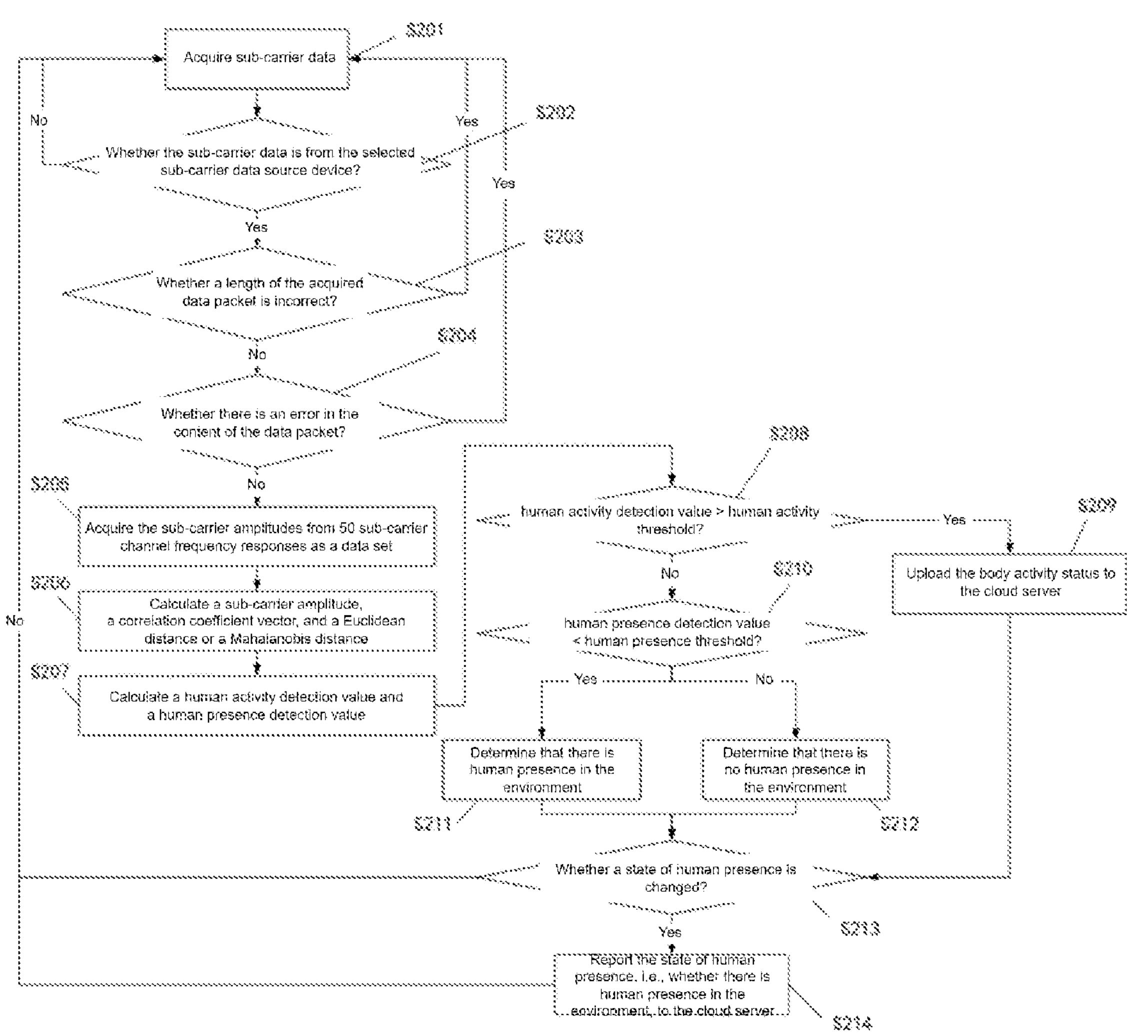
FIG. 6 is a flow chart of performing human body sign detection according to sub-carrier channel frequency response in a preferred embodiment of the Wi-Fi based human body detection method according to the present disclosure.

Referring to FIG. 6, in this embodiment, the Wi-Fi MCU used by the sub-carrier data source device and the smart device is of the same model, such as ESP32, ESP32-S2 and other embedded MCUs, to avoid compatibility issues. Embedded MCUs can obtain more low-level Wi-Fi CSI signals, can obtain all sub-carrier data, up to 306 sub-carriers, and can also obtain current RF base noise, receiving time and antennas. The present disclosure optimizes the algorithm to remove redundant calculations.

Since the human body has the greatest impact on the amplitude of the sub-carriers, the present disclosure mainly analyzes the amplitudes of the sub-carriers. Each channel frequency response of a sub-carrier is represented by two bytes, where the first byte is the imaginary part, and the second byte is the real part, and the amplitude of the sub-carrier a is:

$$a = \sqrt{i^2 + r^2}$$

in which i is the imaginary part of the channel frequency response, and r is the real part of the channel frequency response.

The smart device obtains the sub-carrier amplitude from the stored sub-carrier channel frequency response, and obtains a plurality of data sets by grouping the sub-carrier amplitudes; in each data set, the data set is divided into a plurality of sub-datasets based on different parts of the sub-carrier channel frequency response, and then for each of the sub-datasets, a correlation coefficient between the sub-carrier amplitudes contained in the same sub-dataset is calculated to form a sub-dataset correlation coefficient vector, and the Mahalanobis distance or the Euclidean distance between the sub-carrier amplitudes in the same sub-dataset is calculated to form a sub-dataset distance vector.

Furthermore, a human activity detection value is obtained as an average of the variances of a plurality of sub-dataset correlation coefficient vectors, and a human presence detection value is obtained as an average of the variances of a plurality of sub-dataset distance vectors; in response to the human activity detection value being greater than a human activity threshold value, a state of human activity is determined, and the smart device reports the status to the cloud server; in response to the human body detection value being less than a human body threshold value, a state of human presence is determined, otherwise a state of human absence is determined, and when the smart device detects a change between the state of human presence and the state of human absence, the state is reported to the cloud server.

In this embodiment, the detailed steps for human body detection are included as below.

At step S201, in various detection environments, the smart device in a hybrid mode acquires sub-carriers channel frequency responses on different channels.

At step S202, the smart device checks the acquired data packet of the sub-carrier channel frequency responses, and if the data packet is not from the selected sub-carrier data source device, proceed to step S201. Otherwise, the data packet is stored and processed.

At step S203, the smart device checks whether the length of the acquired data packet of the sub-carrier channel frequency response is incorrect. The total number of bytes of the sub-carriers received on channels in different states is a fixed value. If the total number of bytes of the received data packet is different from the fixed value, the packet is an invalid data packet, and proceed to step S201.

At step S204, the smart device checks whether there is an error in the content of the data packet. The distance between the first three sub-carrier amplitudes in valid channel frequency responses in each part is calculated and determined whether being greater than the distance threshold, and if yes, then the data packet is invalid, and proceed to step S201. The default maximum distance threshold between sub-carrier amplitudes is 8. If the distance is greater than this value, the correlation between sub-carriers is too poor, which may be caused by hardware problems of smart devices, so the corresponding data packet needs to be excluded.

At step S205, the smart device obtains the sub-carrier amplitudes from the saved sub-carrier channel frequency responses, and obtains multiple data sets by grouping the sub-carrier amplitudes, where each obtained 50 packets of valid sub-carriers are grouped into one data set to form a matrix A:

$$A = \begin{bmatrix} a_{11} & a_{12} & \dots & a_{1n} \\ a_{21} & a_{22} & \dots & a_{2n} \\ \vdots & \vdots & \ddots & \vdots \\ a_{m1} & a_{m2} & \dots & a_{mn} \end{bmatrix}, (n = 50)$$

In the above matrix, each row is a valid sub-carrier amplitude, and each sub-carrier vector is denoted as am:

$$a_m = (a_{m1}, a_{m2}, \dots, a_{mn}), (n = 50)$$

wherein, valid sub-carriers are determined by a sub-carrier selection process.

At step S206, the sub-carrier amplitude in matrix A is divided into three parts: LLTF, HT-LTF, and STBC-HT-LTF, and the correlation coefficient between any two sub-carriers forms a correlation coefficient vector $C_i$, the Euclidean distance between any two sub-carriers forms a distance vector $D_i$, $$C_i = (c_1, c_2, \dots, c_n), D_i = (d_1, d_2, \dots, c_n), \\ (n = (m * (m-1)/2), i = 1,2,3)$$

and m is the number of sub-carriers of the channel frequency response in each part.

The channel frequency response includes up to three parts, LLTF, HT-LTF, and STBC-HT-LTF. But due to the different protocols supported by different wireless access points, not in all cases will the channel frequency response include three parts, sometimes it may include only one part, which is LLTF. The specific cases are determined in the sub-carrier selection process.

At step S207, the average of variances of $C_i$ is calculated to obtain the human activity detection value M, the average of variances of $D_i$ is calculated to obtain the human presence detection value H.

At step S208, in response to M being greater than the human activity threshold, it is determined that there is human activity, and proceed to step S209. Otherwise, proceed to step S210.

At step S209, the body activity status is uploaded to the cloud server, and proceed to step 213.

At step S210, in response to H being less than the human presence threshold, proceed to step S211; otherwise, proceed to step S212.

At step S211, it is determined that there is human presence, and proceed to step S213.

At step S212, it is determined that there is human absence, and proceed to step S213.

At step S213, the previous detection state and the current detection state are considered in combination, and in response to there being a transition between a detected state of human presence and a detected state of human absence, go to step S214. Otherwise, go to step S201.

At step S214, the state of human presence or the state of human absence is reported to the cloud server.

The Wi-Fi based human body detection method in the embodiment of the present disclosure can detect the state of human presence, and can further detect the state of human activity, which can expand the application scenarios and application scope of the present disclosure. For example, by combining the state of human activity and the state of human presence, the sleep condition of the human body can be monitored, and the sleep quality can be assessed by the number of human activities during sleep.

Figure 7:
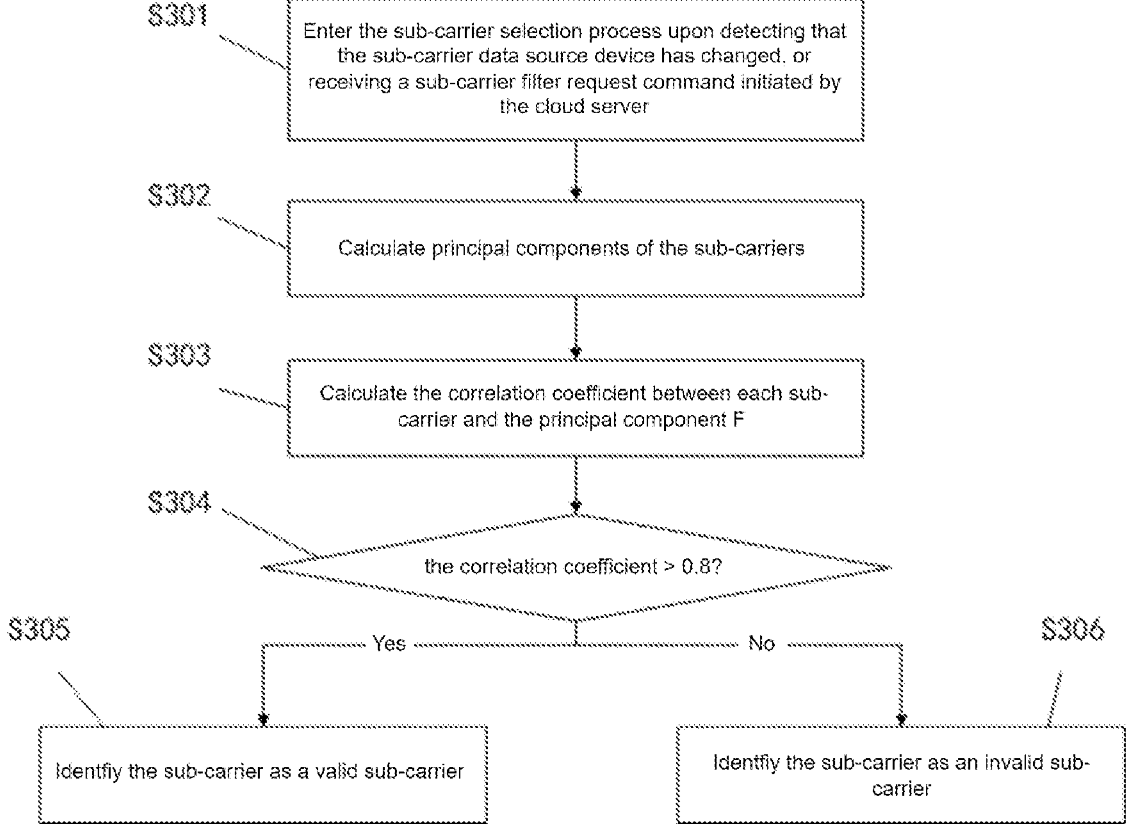
FIG. 7 is a flow chart of a sub-carrier selection process in a preferred embodiment of the Wi-Fi based human body detection method according to the present disclosure.

Referring to FIG. 7, due to the limitations of antennas and physical layers of different wireless access points, not all the data of all sub-carriers can be obtained, or there are errors in the data of sub-carriers. For example, the first four sub-carriers of the sub-carriers received by ESP32 are invalid. In order to apply sub-carrier filtering and perform selection more automatically, in this embodiment, when the smart device detects that the sub-carrier data source device has changed, or receives a sub-carrier filter request command initiated by the cloud server (step S301), the smart device enters the sub-carrier selection process and selects valid sub-carriers for calculation. When the sub-carrier selection process is being processed, it must be ensured that no human is present in the environment, and the process specifically includes the followings.

As shown in step S302, principal components of the sub-carriers are obtained by principal component analysis. Firstly, 500 channel frequency responses of sub-carriers of the current sub-carrier are collected, and the corresponding amplitude data are calculated to form a matrix A:

$$A = \begin{bmatrix} a_{11} & a_{12} & \dots & a_{1n} \\ a_{21} & a_{22} & \dots & a_{2n} \\ \vdots & \vdots & \ddots & \vdots \\ a_{m1} & a_{m2} & \dots & a_{mn} \end{bmatrix}, (n = 500, m = 306)$$

Each row is a sub-carrier amplitude, and each sub-carrier vector is am:

$$a_m = (a_{m1}, a_{m2}, \dots, a_{mn}, (n = 500))$$

The principal component of the matrix is calculated, and the matrix is reduced to a one-dimensional vector to obtain the principal component vector:

$$F = (f_1, f_2, \dots, f_n), (n = 500)$$

Then, in step S303, the correlation coefficient between each sub-carrier am and the principal component F is calculated. In step S304, the determination of the correlation coefficient is completed, and in response to the correlation coefficient being greater than 0.8, then the sub-carrier is identified as a valid sub-carrier in step S305; otherwise, the sub-carrier is identified as an invalid sub-carrier in step S306. Invalid sub-carriers are not involved in subsequent calculations.

Figure 8:
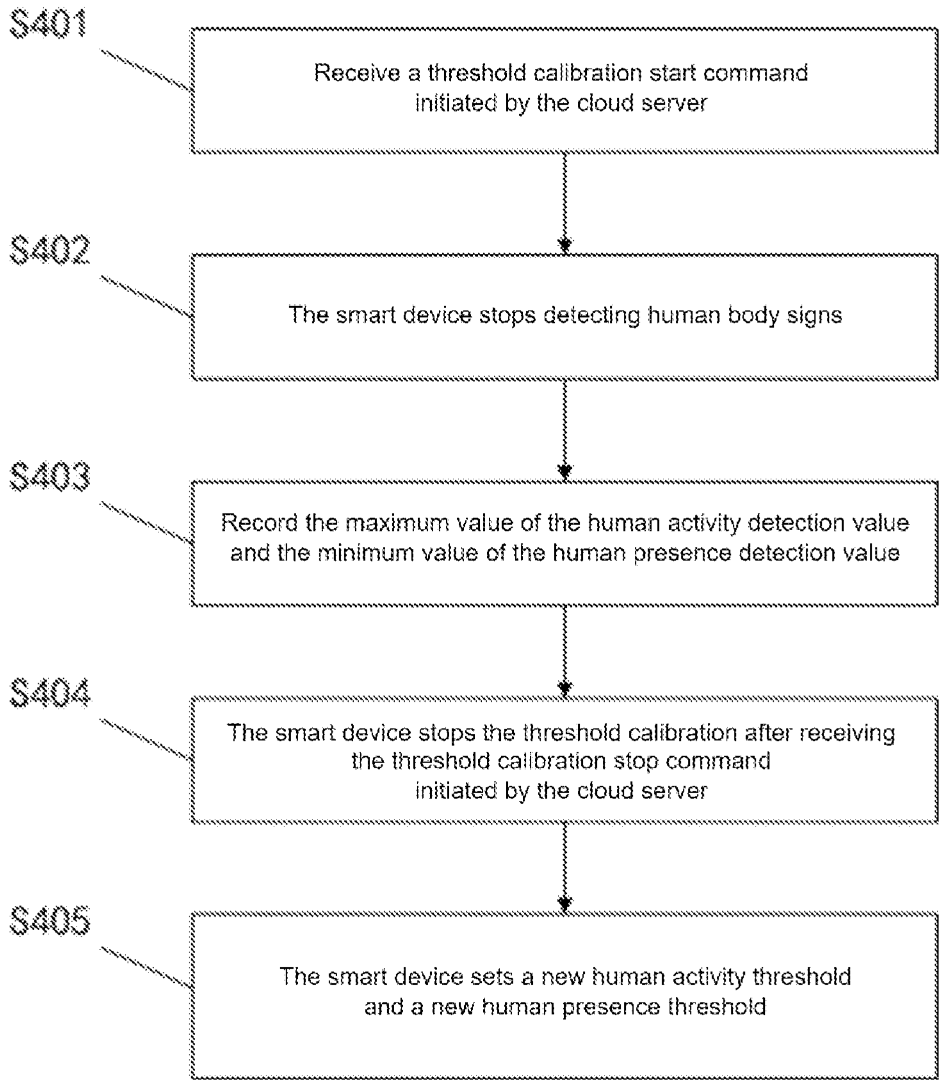
FIG. 8 is a flow chart of threshold calibration for automatic calibration of human activity threshold and human presence threshold in a preferred embodiment of the Wi-Fi based human body detection method according to the present disclosure.

Referring to FIG. 8, in order to make it applicable in different scenarios, the present disclosure further provides a threshold calibration method for automatically calibrating the human activity threshold and human presence threshold in different scenarios. During the calibration, it is necessary to ensure that there is no human in the room and the smart device has been installed to be the same as in the actual test environment. The specific steps include: in step S401, after the smart device receives the threshold calibration start command initiated by the cloud server, it enters the automatic calibration mode in step S402, and the smart device stops detecting human body signs at the time. As shown in step S403, the smart device continuously calculates the human activity detection value and the human presence detection value, and records the maximum value of the human activity detection value and the minimum value of the human presence detection value. After receiving the threshold calibration stop command initiated by the cloud server, the smart device proceeds to step S404, where the smart device stops calculating the human activity detection value and the human presence detection value. In the subsequent step S405, the smart device sets a new human activity threshold and a new human presence threshold. In the specific implementation, the smart device can set the new human activity threshold as the maximum value of the human activity detection value increased by 10%, and set the human presence detection value threshold as the minimum value of the human body detection value decreased by 10%.

In the embodiment of the present disclosure, the interval for sending Ping packet is 5 ms, and 50 data packets are used as a detection data set, which can detect human activities within 200 ms at the fastest, and the 5 ms interval for sending packet has minimal impact on the network environment.

Figure 9:
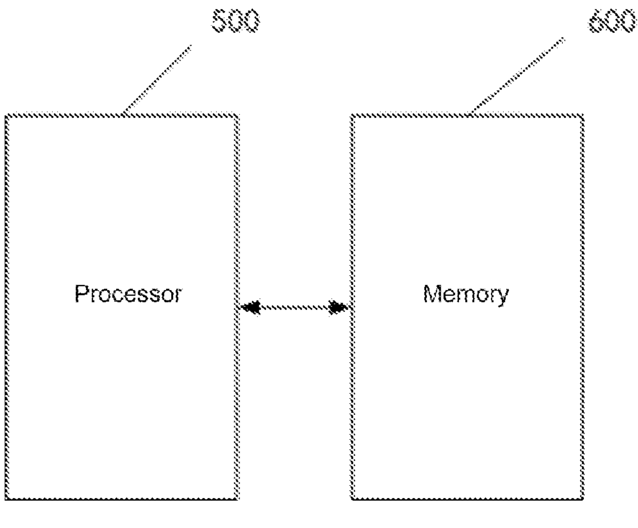
FIG. 9 is a schematic diagram of a preferred embodiment of a Wi-Fi based human body detection smart device according to the present disclosure.

Referring to FIG. 9, a preferred embodiment of the present disclosure further includes a smart device, which includes: a processor 500, a memory 600 and a Wi-Fi transceiver module. The processor 500 executes a program stored in the memory 600, and uses the Wi-Fi transceiver module to complete the steps in the above Wi-Fi based human body detection method.

The above described are only preferred embodiments of the disclosure, and are not intended to limit the scope of the disclosure. Any equivalent structure or equivalent process transformation made by utilizing the contents of the description and drawings of the disclosure, or directly or indirectly applied to other related technical fields are all similarly included in the scope of patent protection of the disclosure.

The invention claimed is:

1. A Wi-Fi based human body detection method, applied to detect a human body sign in an environment by using a change in sub-carrier channel frequency responses in a channel state information of a Wi-Fi connection of a smart device, the method comprising:

selecting, by the smart device, in a plurality of detection environments, a sub-carrier data source device, acquiring the sub-carrier channel frequency responses of the sub-carrier data source device, checking and filtering out invalid sub-carrier channel frequency responses, and storing the sub-carrier channel frequency responses;

the method further comprising:

obtaining, by the smart device, sub-carrier amplitudes from the stored sub-carrier channel frequency responses, and obtaining a plurality of data sets by grouping the sub-carrier amplitudes;

dividing each of the plurality of data sets into a plurality of sub-datasets based on different parts of the sub-carrier channel frequency responses;

for each of the sub-datasets, calculating a correlation coefficient between the sub-carrier amplitudes contained in the same sub-dataset to form a sub-dataset correlation coefficient vector, and calculating a Mahalanobis distance between the sub-carrier amplitudes contained in the same sub-dataset to form a sub-dataset distance vector;

obtaining and taking an average of variances of a plurality of sub-dataset correlation coefficient vectors as a human activity detection value, and obtaining and taking an average of variances of a plurality of the sub-datasets distance vectors as a human presence detection value; and in response to the human activity detection value being greater than a human activity threshold, determining a human activity state;

in response to the human presence detection value being smaller than a human presence threshold, determining a human presence state, and in response to the human presence detection value being greater than or equal to a human presence threshold, determining a human absence state;

the method further comprising a threshold calibration step for automatically calibrating the human activity threshold and the human presence threshold in different scenarios, the threshold calibration step comprising:

after entering an automatic calibration mode, recording and continuously calculating, by the smart device, the human activity detection value and the human presence detection value, and storing a maximum value of the human activity detection value and a minimum value of the human presence detection value until a threshold calibration stop command initiated by a cloud server is received; and after receiving the threshold calibration stop command, setting, by the smart device, a new human activity threshold and a new human presence threshold; wherein the new human activity threshold is greater than the maximum value of the human activity detection value, and the new human presence threshold is smaller than the minimum value of the human presence detection value.

2. The Wi-Fi based human body detection method according to claim 1, further comprising: in response to the smart device determining the human activity state, reporting the human activity state to the cloud server.

3. The Wi-Fi based human body detection method according to claim 1, further comprising: in response to the smart device detecting a change between the human presence state and the human absence state, reporting the human presence state to the cloud server.

4. The Wi-Fi based human body detection method according to claim 1, further comprising: when the smart device generates the sub-dataset distance vector, forming, by the smart device, the sub-dataset distance vector by calculating a Euclidean distance between the sub-carrier amplitudes included in the same sub-dataset.

5. The Wi-Fi based human body detection method according to claim 1, wherein the smart device checking and filtering out invalid sub-carrier channel frequency responses further comprises: calculating, by the smart device, a distance between first three sub-carriers amplitudes in different parts of the sub-carrier channel frequency response, and in response to the distance being greater than a distance threshold, determining the sub-carrier channel frequency response as invalid.

6. The Wi-Fi based human body detection method according to claim 5, wherein the distance threshold is 8.

7. The Wi-Fi based human body detection method according to claim 1, wherein each of the data sets comprises 50 sub-carrier amplitudes.

8. The Wi-Fi based human body detection method according to claim 1, wherein the detection environment comprises:

a smart device, and a wireless access point as a sub-carrier data source;

wherein the method further comprises: continuously sending, by the smart device, Ping packets to the wireless access point, and receiving the sub-carrier channel frequency response carried in Ping Replay packets returned by the wireless access point.

9. The Wi-Fi based human body detection method according to claim 1, wherein the detection environment comprises:

a plurality of smart devices, and a wireless access point as a sub-carrier data source;

wherein the method further comprises: continuously sending, by the smart device, Ping packets to the wireless access point, and receiving from the wireless access point the sub-carrier channel frequency responses carried in Ping Replay packets returned by other smart devices.

10. The Wi-Fi based human body detection method according to claim 1, wherein the detection environment comprises:

one or more smart devices, and a packet-sending device as the sub-carrier data source;

wherein the method further comprises: by the packet-sending device, constantly switching channels and continuously sending Ping packets; acquiring, by the smart device, the sub-carrier channel frequency response from the Ping packets.

11. The Wi-Fi based human body detection method according to claim 1, further comprising a process of selecting the sub-carrier data source device by the smart device, which comprises:

turning on, by the smart device, a hybrid mode and binding the wireless access point as the sub-carrier data source device by default;

in response to the smart device receiving data from a packet-sending device, binding the packet-sending device as the sub-carrier data source device; and in response to the smart device receiving a binding command from the cloud server, binding a device specified in the binding command as the sub-carrier data source device.

12. The Wi-Fi based human body detection method according to claim 1, further comprising a sub-carrier selection step comprising:

in response to there being no human presence in the environment, collecting, by the smart device, the sub-carrier channel frequency responses for multiple times for each sub-carrier, and forming the sub-carrier amplitude vector based on the sub-carrier amplitudes corresponding to the sub-carrier channel frequency responses of each time, and then forming a sub-carrier amplitude matrix from all the sub-carrier amplitude vectors;

reducing the sub-carrier amplitude matrix into a one-dimensional principal component vector by using a principal component analysis algorithm; and calculating a correlation coefficient between each of the sub-carrier amplitude vectors and the principal component vector, and in response to the correlation coefficient being greater than a valid sub-carrier threshold, determining the corresponding sub-carrier as a valid sub-carrier;

wherein the smart device is configured to only group the sub-carrier amplitudes corresponding to the sub-carriers selected by the sub-carrier selection step, and put them into the data set; in response to the smart device detecting a change of the sub-carrier data source device, or receiving a sub-carrier filtering request command initiated by the cloud server, the smart device is configured to start the sub-carrier selection step.

13. The Wi-Fi based human body detection method according to claim 12, further comprising: collecting, by the smart device, the sub-carrier channel frequency responses for 500 times for each sub-carrier.

14. The Wi-Fi based human body detection method according to claim 1, the threshold calibration step further comprising:

in response to there being no human presence in the environment, enabling the smart device to enter the automatic calibration mode in response to the smart device receiving a threshold calibration start command from the cloud server; wherein in the automatic calibration mode, the smart device does not perform a human body sign detection.

15. The Wi-Fi based human body detection method according to claim 14, wherein the new human activity threshold is the maximum value of the human activity detection value increased by 10%, and the new human presence threshold is the minimum value of the human presence detection value decreased by 10%.

16. A non-transitory computer-readable medium comprising a computer program, which when run on a processor, causes the processor to implement the WiFi-based human body detection method according to claim 1.

17. The non-transitory computer-readable medium according to claim 16, wherein the smart device checking and filtering out invalid sub-carrier channel frequency responses further comprises: calculating, by the smart device, a distance between first three sub-carriers amplitudes in different parts of the sub-carrier channel frequency response, and in response to the distance being greater than a distance threshold, determining the sub-carrier channel frequency response as invalid.

18. The non-transitory computer-readable medium according to claim 16, the processor is caused to further implement a process of selecting the sub-carrier data source device by the smart device, which comprises:

turning on, by the smart device, a hybrid mode and binding the wireless access point as the sub-carrier data source device by default;

in response to the smart device receiving data from a packet-sending device, binding the packet-sending device as the sub-carrier data source device; and in response to the smart device receiving a binding command from the cloud server, binding a device specified in the binding command as the sub-carrier data source device.

19. The non-transitory computer-readable medium according to claim 16, the processor is caused to further implement a sub-carrier selection step; wherein the smart device only groups the sub-carrier amplitudes corresponding to the sub-carriers selected by the sub-carrier selection step, and puts them into the data set; in response to the smart device detecting a change of the sub-carrier data source device, or receiving a sub-carrier filtering request command initiated by the cloud server, the smart device starts the sub-carrier selection step, and the sub-carrier selection step comprises:

in response to there being no human presence in the environment, collecting, by the smart device, the sub-carrier channel frequency responses for multiple times for each sub-carrier, and forming the sub-carrier amplitude vector based on the sub-carrier amplitudes corresponding to the sub-carrier channel frequency responses of each time, and then forming a sub-carrier amplitude matrix from all the sub-carrier amplitude vectors;

reducing the sub-carrier amplitude matrix into a one-dimensional principal component vector by using a principal component analysis algorithm; and calculating a correlation coefficient between each of the sub-carrier amplitude vectors and the principal component vector, and in response to the correlation coefficient being greater than a valid sub-carrier threshold, determining the corresponding sub-carrier as a valid sub-carrier.

20. The non-transitory computer-readable medium according to claim 16, the processor is caused to further implement:

in response to there being no human presence in the environment, enabling the smart device to enter the automatic calibration mode in response to the smart device receiving a threshold calibration start command from the cloud server; wherein in the automatic calibration mode, the smart device does not perform a human body sign detection.

* * * * *